(12) United States Patent
Schröder

(10) Patent No.: US 6,203,777 B1
(45) Date of Patent: Mar. 20, 2001

(54) METHOD OF CONTRAST ENHANCED MAGNETIC RESONANCE IMAGING USING CARBOHYDRATE PARTICLES

(75) Inventor: Ulf Schröder, Lund (SE)

(73) Assignee: Nycomed Imaging AS, Oslo (NO)

( * ) Notice: Subject to any disclaimer, the term of this patent is extended or adjusted under 35 U.S.C. 154(b) by 0 days.

(21) Appl. No.: 08/879,148

(22) Filed: Jun. 19, 1997

Related U.S. Application Data

(62) Continuation of application No. 08/467,021, filed on Jun. 6, 1995, now Pat. No. 5,720,939, which is a continuation-in-part of application No. 08/043,982, filed on Apr. 7, 1993, now abandoned, which is a continuation of application No. 07/888,305, filed on May 27, 1992, now abandoned, which is a continuation of application No. 07/693,031, filed on Apr. 30, 1991, now abandoned, which is a continuation of application No. 07/278,326, filed on Nov. 30, 1988, now abandoned, which is a continuation of application No. 06/775,047, filed as application No. PCT/SE84/00437 on Dec. 20, 1984, now abandoned.

(30) Foreign Application Priority Data

Dec. 21, 1983 (SE) .................................................. 8307060

(51) Int. Cl.$^7$ .................................................. A61B 5/055
(52) U.S. Cl. .................................. 424/9.322; 424/9.323; 514/54; 514/57; 514/59; 600/420
(58) Field of Search ........................... 424/9.322, 9.323; 436/173; 514/54, 57, 59; 600/420

(56) References Cited

U.S. PATENT DOCUMENTS

| | | | |
|---|---|---|---|
| 4,247,406 | * | 1/1981 | Widder et al. .................. 252/62.53 |
| 4,276,885 | * | 7/1981 | Tickner et al. ........................ 128/660 |
| 4,501,726 | * | 2/1985 | Schröder et al. ........................ 424/1.1 |
| 4,544,545 | * | 10/1985 | Ryan et al. ............................ 424/1.1 |
| 4,572,203 | * | 2/1986 | Feinstein ............................... 128/661 |
| 4,687,748 | * | 8/1987 | Schröder .............................. 436/526 |
| 4,713,249 | * | 12/1987 | Schröder .............................. 424/488 |
| 4,767,611 | * | 8/1988 | Gordon ..................................... 424/9 |
| 4,985,233 | * | 1/1991 | Klaveness et al. ....................... 424/9 |
| 4,986,980 | * | 1/1991 | Jacobsen .................................. 424/9 |
| 5,720,939 | * | 2/1998 | Schröder ............................ 424/9.322 |

* cited by examiner

Primary Examiner—Gary E. Hollinden
(74) Attorney, Agent, or Firm—Lyon & Lyon LLP

(57) ABSTRACT

In a method of contrast MR imaging, using parenterally administered contrast agents, the improvement comprising using as the contrast agent, e.g. to achieve a negative contrast effect, composite particles comprising a biotolerable, carbohydrate or carbohydrate derivative, preferably polymeric, matrix material containing magnetically responsive particles, eg. of magnetite.

9 Claims, 16 Drawing Sheets

METHOD OF CONTRAST ENHANCED MAGNETIC RESONANCE IMAGING USING CARBOHYDRATE PARTICLES

This is a continuation of application Ser. No. 08/467,021, filed on Jun. 6, 1995, U.S. Pat. No. 5,720,939, itself a continuation-in-part of application Ser. No. 08/043,982 filed Apr. 7, 1993, abandoned, itself a continuation of application Ser. No. 07/888,305 filed May 27, 1992, abandoned, itself a continuation of application Ser. No. 07/693,031 filed Apr. 30, 1991, abandoned, itself a continuation of application Ser. No. 07/278,326 filed Nov. 30, 1988, abandoned, itself a continuation of application Ser. No. 06/775,047 filed Aug. 15, 1985, abandoned, which was filed under 35 U.S.C. §371 based on International Application No. PCT/SE84/00437, filed on Dec. 20, 1984, all of which are expressly incorporated herein by reference.

BACKGROUND

The invention relates to a method of contrast enhanced magnetic resonance imaging (MRI), and in particular to the use of magnetic particles as diagnostic contrast agents in MRI.

In diagnostic medicine, contrast agents are today being used primarily in X-ray diagnostics whore an increased contrast effect is obtained during examination of, for example, internal organs, such as the kidneys, the urinary tract, the digestive tract, the vascular system of the heart (angiography), etc. This contrast effect is based upon the fact that the contrast agent itself is less permeable to X-rays than the surrounding tissue, as a result of which a different blackening of the X-ray plate is obtained.

X-raying implies certain radiation hazards, but during angiography the complication risk is associated in particular with the use of contrast agents.

In recent years, a number of now methods have been introduced in diagnostic radiology. One such method goes by the name NMR (Nuclear Magnetic Resonance) which provides information not only about the distribution of the water content in a specific tissue (in contradistinction to radiology which merely gives a measure of the transmissibility of the X-rays in a specific tissue), but also about the chemical tissue structure which is different in normal and pathological tissue.

In the NMR method, a strong and homogeneous magnetic field is applied across the tissue to be examined. By studying the so-called relaxation times of the protons of the molecules present, especially the protons of the water, it is possible to produced via comprehensive and complex computer calculations, a visual image of the structure of the tissue concerned. (This technique is now commonly referred to as magnetic resonance imaging or MRI).

There is, however, an interest in being able to make a differential diagnosis between pieces of tissue having a high density of blood vessels and, alternatively, tissue having a low density of vessels. Such a situation which has considerable clinical interest, comprises the localisation of tumours which, in their periphery, have a higher density of vessels as compared with normal tissue.

One useful method in this context is to inject into the vascular system particles responsive to a magnetic field and showing changes in the above-mentioned relaxation times.

By "magnetic particles" or "magnetically responsive particles" as used herein is meant particles of materials, such as magnetite, which have a Curie temperature and thus are ferromagnetic, ferrimagnetic or, at sub-domain size, superparamagnetic. Superparamagnetic particles exhibit the cooperative magnetic effects of ferri- or ferromagnetism when exposed to magnetic fields but, being sub-domain size, lose their magnetization in the absence of the field. Magnetite particles of 10–20 nm size for example are superparamagnetic.

These magnetic particles interfere with the above-mentioned homogeneous magnetic field in that there is formed, around each individual particle, a field gradient which in its turn changes the relaxation times of nearby protons causing a fall-off in MR signal intensity. Put more simply, this means that "black holes" are formed around each particle which may be visualized and thus give an impression of the vessel density in the tissue in question.

SUMMARY OF THE INVENTION

Thus viewed from one aspect the invention provides a method of contrast enhanced nuclear magnetic resonance diagnostic imaging which comprises administering into the vascular system of a subject a contrast enhancing amount of a nuclear magnetic resonance imaging contrast agent and generating an image of said subject, the improvement comprising administering as said contrast agent composite particles comprising a biotolerable, carbohydrate or carbohydrate derivative matrix material (preferably a polymeric material and especially preferably an endogenous carbohydrate material) containing magnetically responsive particles, said magnetically responsive particles being of a material having a Curie temperature, said composite particles preferably having a maximum dimension (diameter) below 1 $\mu$m. eg. from 0.010 to 1 $\mu$m.

DETAILED DESCRIPTION

Figure 1:
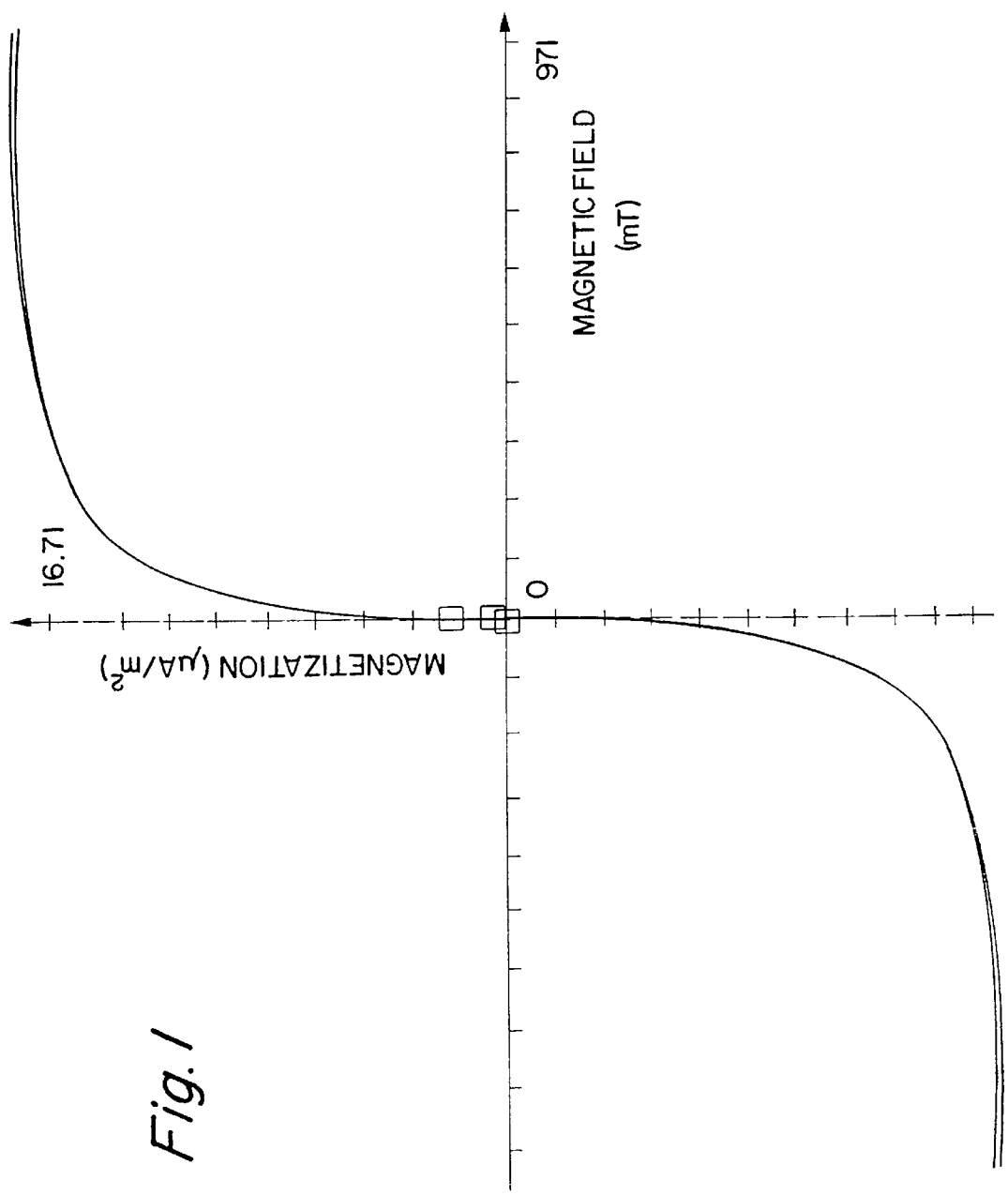
FIG. 1 is a plot of the magnetization curve for the composite particles of Example 4 below (the numbers given on the axes are the maximum values of magnetization (in $\mu A/m^2$) and magnetic field (in mT) attained)

When using magnetic particles in MR imaging, it is desired, in order to achieve optimal conditions, to be able to vary the amount of magnetically responsive material, without affecting on that account the pharmacodynamic and circulatory characteristics of the particles. To be able to do this, one may use a technique which implies enclosing the responsive material in a matrix, preferably a matrix of spherical shape, and the matrix should per se satisfy the following criteria:

biocompatible biologically degradable nonimmunogenic.

A matrix of this type normally is built up of some type of polymers which are held together by chemical bonds. Different types of polymers are available for making such matrices. However, the selection of polymers will be very limited if the above-mentioned criteria of the matrix are to be fulfilled.

One type of polymers that has proved useful in these contexts are the carbohydrates, especially those which are included in the body as a natural constituent.

Monomeric and oligomeric carbohydrate materials may also be used as the matrix material.

Endogenous carbohydrates are represented by starch and glycogen, but also dextran may be included in this group because of its prolonged use as a blood substituent in medical service.

The production of a carbohydrate matrix satisfying these criteria is described in U.S. Pat. No. 4,501,726 (Schröder et al.), U.S. Pat. No. 4,687,748 (Schröder) and U.S. Pat. No. 4,713,249 (Schröder). The carbohydrate polymers referred to in these three U.S. patents are starch, glycogen, pullullan, agarose, cellulose, alginate, chitosan, carrageenan, heparin, dextran and dextrin, and derivatives thereof. For the present invention, heparin, or more especially a heparin analog such as chondroitin-4-sulphate, is the preferred matrix material.

Other carbohydrates referred to include glucose, maltose and lactose. These patents also describe the production of such composite particles wherein the magnetic particles are particles of materials such as Ni—NiO, Ni—$TiO_4$, Mn—Zn, Ferrite, Ni, Ferrofluid, Magnetite ($Fe_3O_4$), etc.

It is in this connection extremely advantageous if covalent cross-linking of carbohydrate polymers can be avoided in the production of a useful matrix. For example, covalently cross-linked carbohydrate matrices have been found to produce transformed cells, in the form of granuloma, when used on humans (Am. Surg. 142: 1045 (1955)).

There are, however, for certain systems no alternatives to the covalent cross-linking, especially when-using combinations of different polymers and cross-linking agents in order to obtain a useful system. As an example, it is possible to cross-link starch with acrylates and, alternatively, to cross-link acrylic polymers with starch.

Another factor of importance to the injection of composition particles into the vascular system is that the particles have a size that prevents them from getting stuck in the capillary system of different tissues during the first passage. To prevent this, the particles should have a diameter or maximum dimension below 1 μm (Chem.Pharm.Bull. 23: 1452 (1975)) and preferably a surface structure of hydrophilic character.

When particles are injected into the vascular system, after a given period of time all the particles will have collected in the liver or spleen (the RES system) because the normal function of these organs is to purify the blood of foreign particles. At present, there is only one method described which is capable of collecting particles at organs other than those mentioned above, and this is by utilising magnetically responsive particles.

This is of particular interest in the context of this invention because the composite particles containing magnetically responsive particles can be made to stop in different tissues by means of an external magnetic field. When the magnetically responsive particles then are stuck in the desired tissue, the tissue in question can simply be visualised by means of the NMR method referred to above.

One matrix material for use in the context of this invention consists of carbohydrates that have been stabilised by crystallization, which means that the type of chemical bonds holding the polymeric network together is not covalent in character, mainly hydrogen bonds, van der Waals forces or, in some cases, ion bonds.

As carbohydrates, use may be made of all conceivable variants, including carbohydrates of varying molecular weight and/or substituted or otherwise derivatised carbohydrates. For example, it may be mentioned that it is possible to produce and use carbohydrate/magnetically responsive particle composite particles in which the carbohydrate is of starch origin running from relatively low-molecular weight materials of the dextrin type etc., up to materials such as native potato starch which have a molecular weight of several millions. The same molecular weight range is applicable to other groups of carbohydrates such as dextran or glycogen.

The composite particles of the invention may be used in other imaging modalities and in therapy. Thus in another diagnostic method, use may be made of the movability of magnetically responsive particles in a tissue. The basic principle of this method may be studied according to the following: if magnetically responsive particles are introduced into a magnetic field, the particles will align themselves in the direction of the field lines. If the field is removed or shut down, the magnetically responsive particles will change their position in response to processes in the tissue. The duration of this change may, however, vary between different tissues and also in dependence upon the localisation of the particles within the tissue in question. This variability of the response of the magnetic material may be utilised diagnostically. If magnetically responsive particles are administered to a patient, the distribution of the particles in different organs can be determined by means of a sensitive magnetometer capable of detecting above-mentioned changes (Nature 302: 336 (1983)).

Ultrasonic imaging is another visualisation technique which can be used. Here sound-waves are reflected differently by different types of tissue, depending upon the acoustic impedance of these tissues. Also in this respect, there is interest in being able to use some type of contrast agent in order to obtain an improved contrast for specific organs. Particles of different types have here been shown to provide changed echo effects and a changed resolution associated therewith (J. Acoust.Soc.Am. 74: 1006 (1983)).

It is also possible to use magnetically responsive particles having a Curie point, ie. Curie temperature, of about 42° C. in the treatment of hypothermia. In this instance, the magnetically responsive particles are retained during the treatment of the hypothermia by a magnetic field, but the moment the tissue temperature exceeds the Curie point, the particles disappear from the tissue because the magnetic responsiveness disappears at this temperature.

By labelling the particles with some gamma-radiating nuclide (for example technetium-99m) it is possible to localise the particles by means of a gamma camera and hereby also to combine this examination with some of the other techniques referred to above.

The following non-limiting Examples are provided to illustrate the main features of the invention.

EXAMPLE 1—Dextran Matrix

Dextran spheres having a size of about 1 μm with enclosed magnetite particles (size 10–20 nm) were suspended in human serum. The relaxation times of the solution were measured with an NMR apparatus (Praxis II, Alnor Instrument AB, Nyköping) and compared with the relaxation times for the same serum without magnetically responsive dextran spheres. The following values of $T_1$ and $T_2$, respectively, were obtained.

|  |  | $T_1$ (ms) | $T_2$ (ms) |
|---|---|---|---|
| Serum without particles: |  | 1660 | 400 |
| Serum with particles: conc | 0.05 mg/ml | 1342 | 109 |
|  | 0.1 mg/ml | 1306 | 82.2 |
|  | 0.2 mg/ml | 1147 | 52.6 |
|  | 0.5 mg/ml | 968 | 30.7 |
|  | 1.0 mg/ml | 813 | 24.0 |
|  | 2.0 mg/ml | 688 | 19.9 |
|  | 4.0 mg/ml | 691 | 22.9 |

EXAMPLE 2—Dextran Particles

Dextran (5 g, Pharmacia AB, Uppsala, Sweden) having a mean molecular weight of 40,000 was dissolved in water (10 ml). At a temperature of 60° C., $FeCl_3.6H_2O$ (1.35 g) and $FeCl_2.4H_2O$ (0.81 g) was dissolved in the carbohydrate solution whereafter the mixture was slowly precipitated into 0.18M NaOH (100 ml) at 60° C. while sonicating. The sonication was allowed to continue for another 10 minutes followed by a centrifugation at 4000 rpm for 5 minutes. The supernatant was collected and a fraction dialysed against 0.9% NaCl (5×1 l). A magnetization curve revealed that the dextran particles were superparamagnetic and they exhibit a mean hydrodynamic diameter of 560 nm.

EXAMPLE 3—Magnetite Particles

Magnetite particles were precipitated from an aqueous solution (500 ml) of $FeCl_2.4H_2O$ (12.50 g, 62.9 mmol) and $FeCl_3.6H_2O$ (33.99 g, 126 mmol) by quick addition of $NH_4OH$ to pH above 10 while stirring vigorously. The particles wore collected magnetically and washed with water to pH below 6. The particles were dispersed in approximately 200 ml of water.

EXAMPLE 4—Dextran Particles

A dispersion of magnetite particles (Example 3, 0.5 g magnetite particles) was diluted with water (85 ml) and to this as added dextran with a mean molecular weight of 40,000 (100 mg, Pharmacia AB, Uppsala, Sweden) dissolved in water (10 ml). The dispersion was sonicated and centrifuged. The supernatant was collected. A magnetization curve (FIG. 1) revealed that the dextran particles were superparamagnetic and they exhibit a mean hydrodynamic diameter of 260 nm.

EXAMPLE 5—Dextran Derivative Particles

Figure 2:
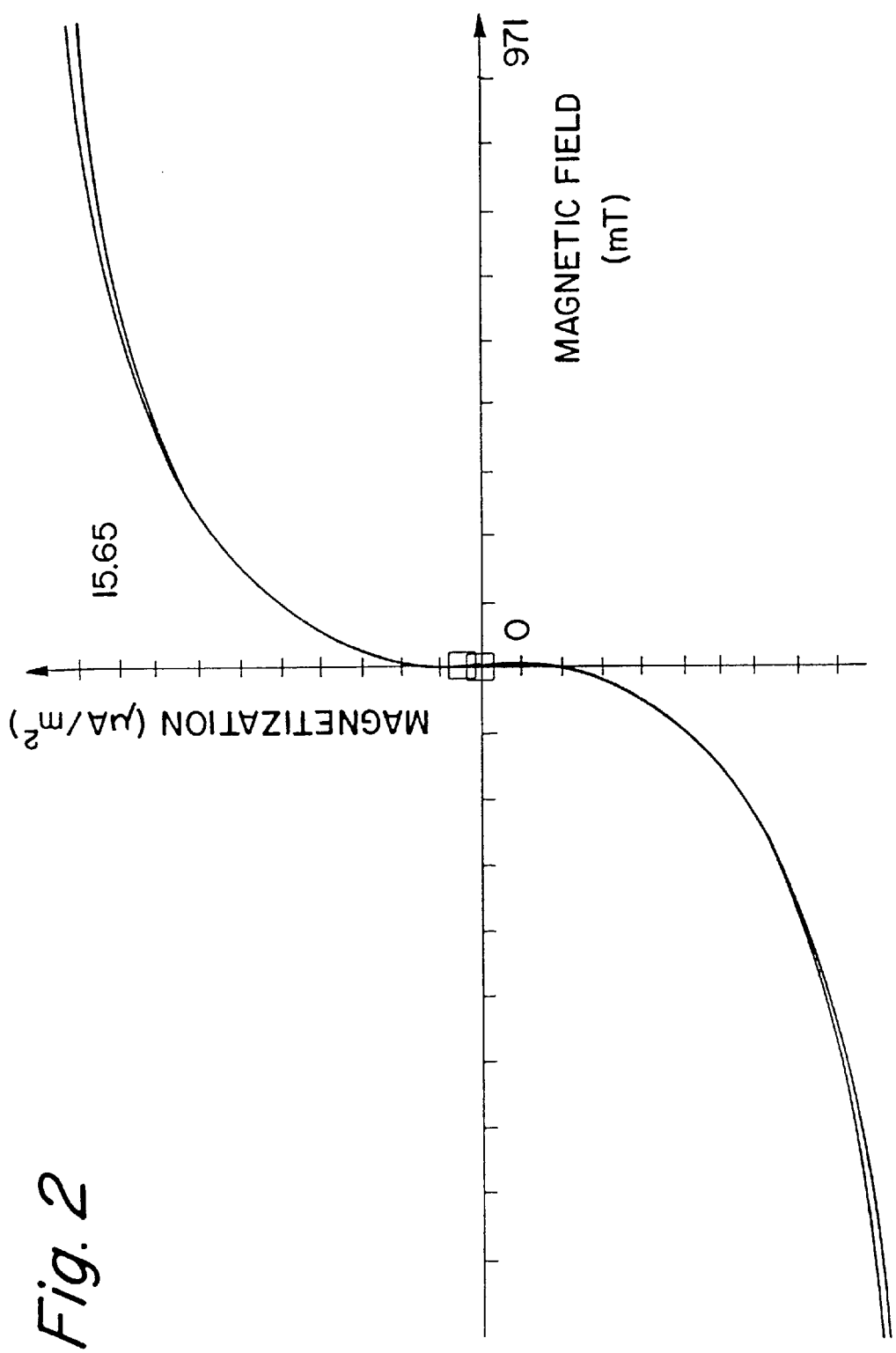
FIG. 2 is a plot of the magnetization curve for the composite particles of Example 5 below.

Carboxymethyldextran with a mean molecular weight of 65,000 (0.5 g, Pharmacia, Uppsala, Sweden) was dissolved in water (10 ml). At a temperature of 60° C., $FeCl_3.6H_2O$ (1.35 g) and $FeCl_2.4H_2O$ (0.81 g) was dissolved in the carbohydrate solution whereafter the mixture was slowly precipitated into 0.18M NaOH (100 ml) at 60° C. while sonicating. The sonication was allowed to continue for another 10 minutes followed by a centrifugation at 4000 rpm for 5 minutes. The supernatant was collected. A magnetization curve (FIG. 2) revealed that the carboxymethyldextran particles were superparamagnetic and they exhibit a mean hydrodynamic diameter of 180 nm.

EXAMPLE 6—Dextran Derivative Particles

A dispersion of magnetite particles (Example 3a, 0.5 g magnetite particles) was diluted with water (85 ml) and to this was added carboxymethyldextran with a mean molecular weight of 65,000 (50 mg, Pharmacia AD, Uppsala, Sweden) dissolved in water (5 ml). The dispersion was sonicated, centrifuged and the supernatant filtered through 0.45 μm filter. A magnetization curve revealed that the carboxymethyldextran particles were superparamagnetic and they exhibit a mean hydrodynamic diameter of 69 nm.

EXAMPLE 7—Dextran Derivative Particles

DEAE-dextran (1.5 g, Pharmacia AB, Uppsala, Sweden) having a mean moleculare weight of 500,000 was dissolved in water (10 ml). At a temperature of 60° C., $FeCl_3.6H_2O$ (1.35 g) and $FeCl_2.4H_2O$ (0.81 g) was dissolved in the carbohydrate solution whereafter the mixture was slowly precipitated into 0.18M NaOH (100 ml) at 60° C. while sonicating. The sonication was allowed to continue for another 10 minutes followed by a centrifugation at 4000 rpm for 5 minutes. The supernatant was collected. A magnetization curve revealed that the DEAE-dextran particles were superparamagnetic and they exhibit a mean hydrodynamic diameter of 140 nm.

EXAMPLE 8—Dextran Derivative Particles

Figure 3:
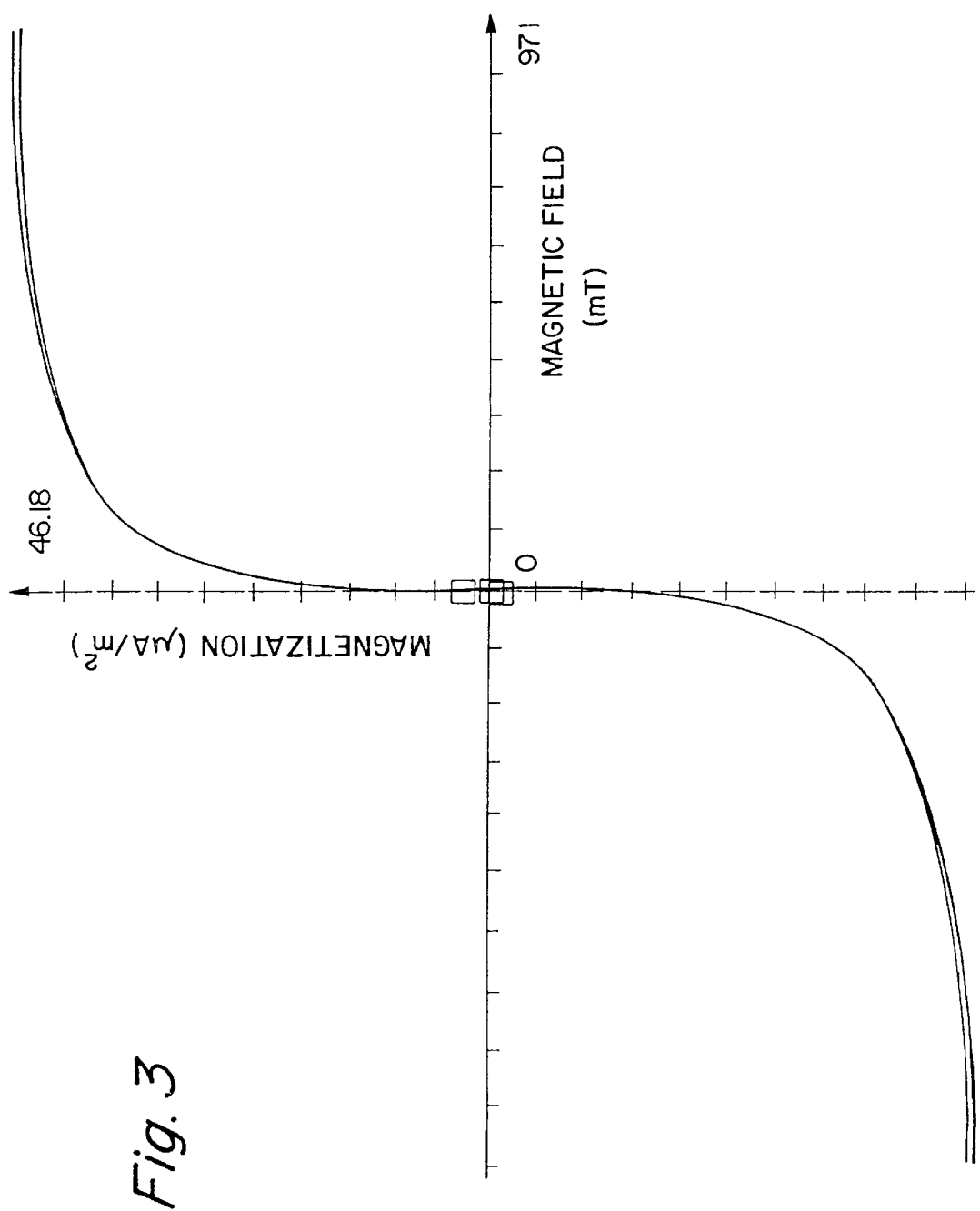
FIG. 3 is a plot of the magnetization curve for the composite particles of Example 8 below.

A dispersion of magnetite particles (Example 3, 0.5 g magnetite particles) was diluted with water (85 ml) and to this was added DEAE-dextran having a mean molecular weight of 500,000 (50 mg, Pharmacia Ab, Uppsala, Sweden) dissolved in water (5 ml). The dispersion was sonicated, centrifuged and the supernatant filtered through a 0.22 μm filter. A magnetization curve (FIG. 3) revealed that the DEAE-dextran particles were superparamagnetic and they exhibit a mean hydrodynamic diameter of 76 nm.

EXAMPLE 9—Dextran Derivative Particles

Figure 4:
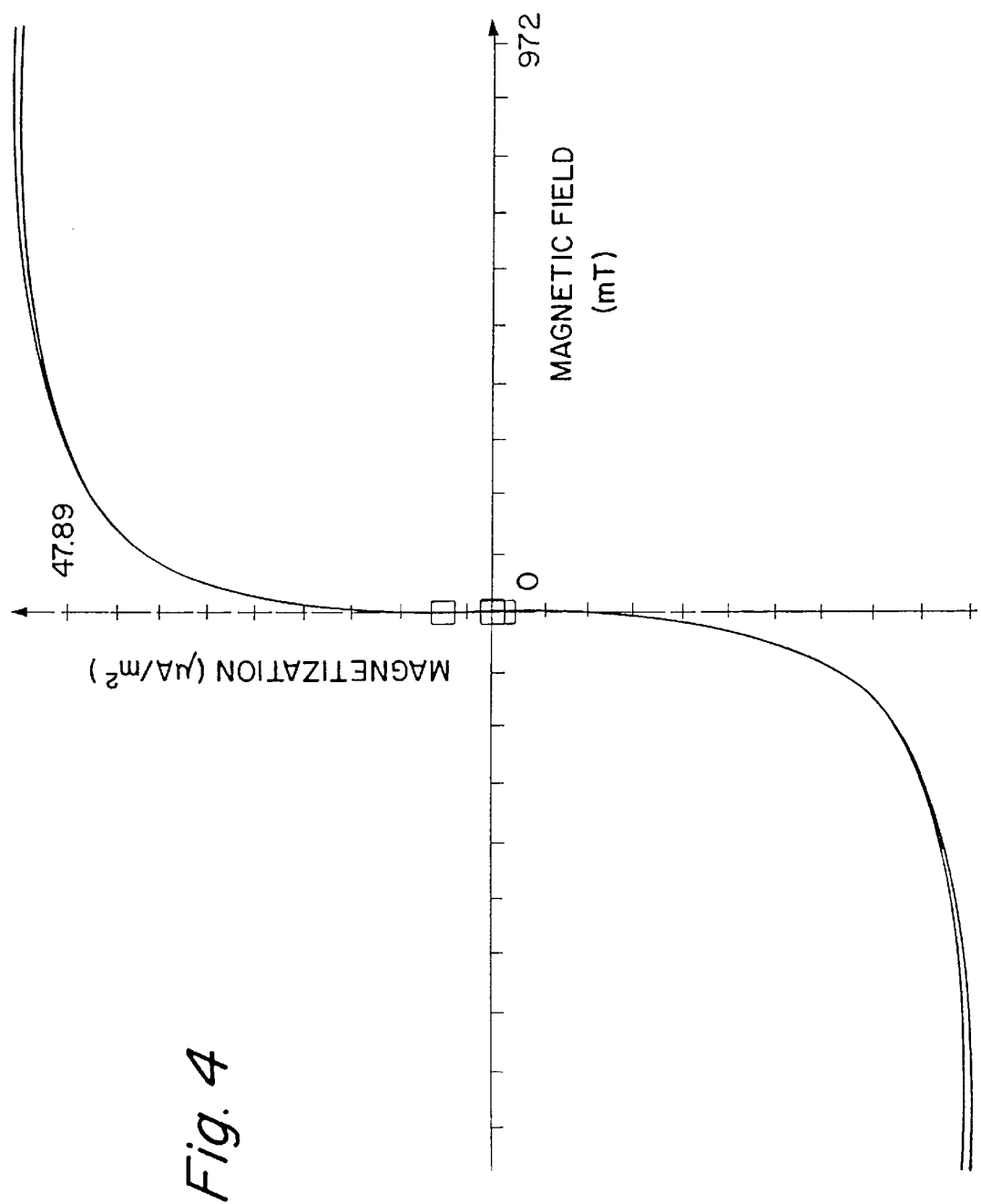
FIG. 4 is a plot of the magnetization curve for the composite particles of Example 9 below.

A dispersion of magnetite particles (Example 3, 0.5 g magnetite particles) was diluted with water (85 ml) and to this was added dextranphosphate with a mean molecular weight of 74,000 (50 mg, Pharmacia AB, Uppsala, Sweden) dissolved in water (5 ml). The dispersion was sonicated, centrifuged and the supernatant filtered through 0.22 μm filter. A magnetization curve (FIG. 4) revealed that the dextranphosphate particles were superparamagnetic and they exhibit a mean hydrodynamic diameter of 74 nm.

EXAMPLE 10—Dextran Derivative Particles

Figure 5:
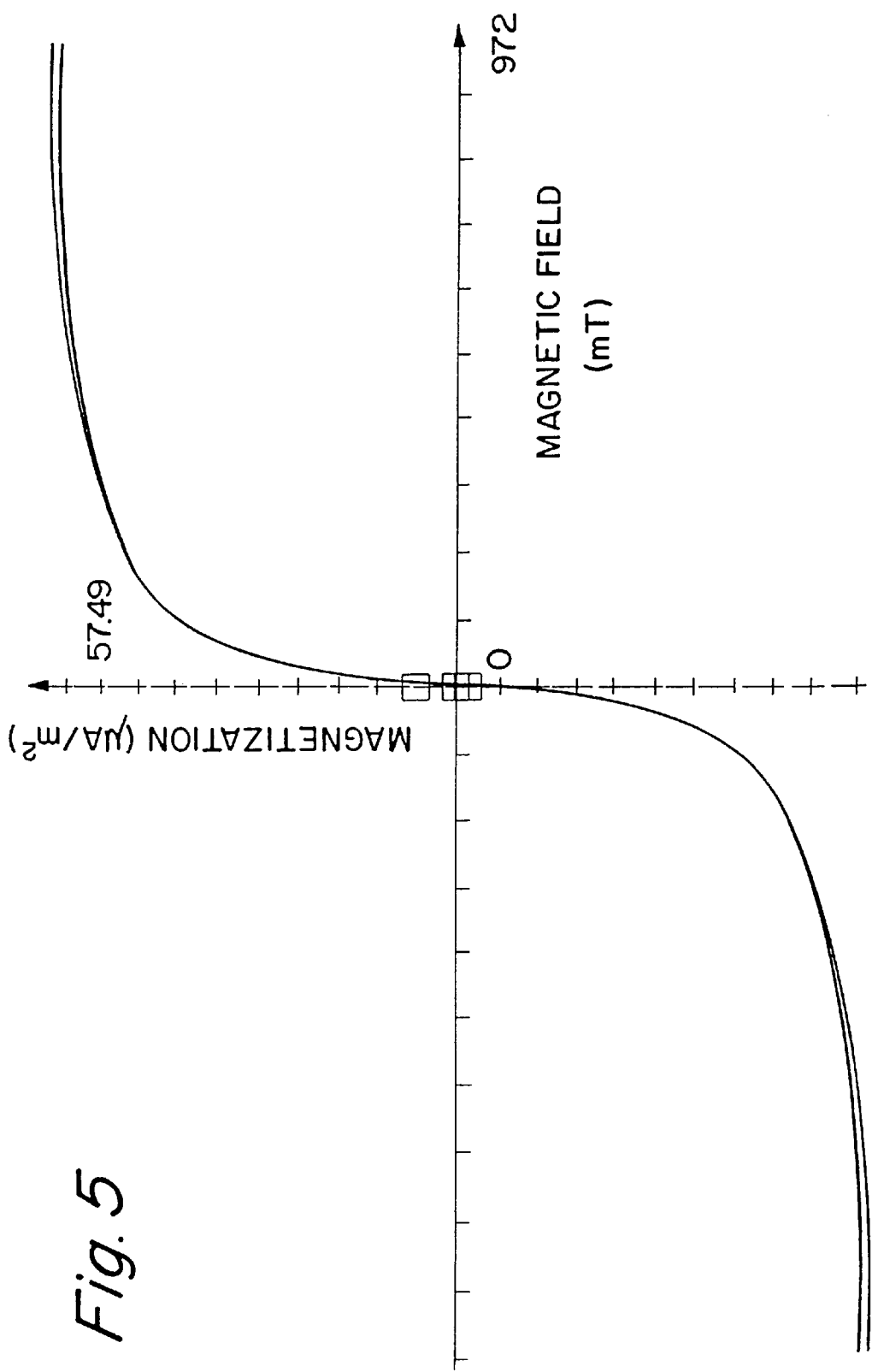
FIG. 5 is a plot of the magnetization curve for the composite particles of Example 10 below.

A dispersion of magnetite particles (Example 3, 0.25 g magnetite particles) was diluted with water (45 ml) and to this was added dextransulphate having a mean molecular weight of 500,000 (25 mg, Sigma, D 7037) dissolved in water. The dispersion was sonicated and centrifuged. The supernatant was collected. A magnetization curve (FIG. 5) revealed that the dextransulphate particles were superparamagnetic and they exhibit a mean hydrodynamic diameter of 85 nm.

EXAMPLE 11—Heparin Particles

Figure 6:
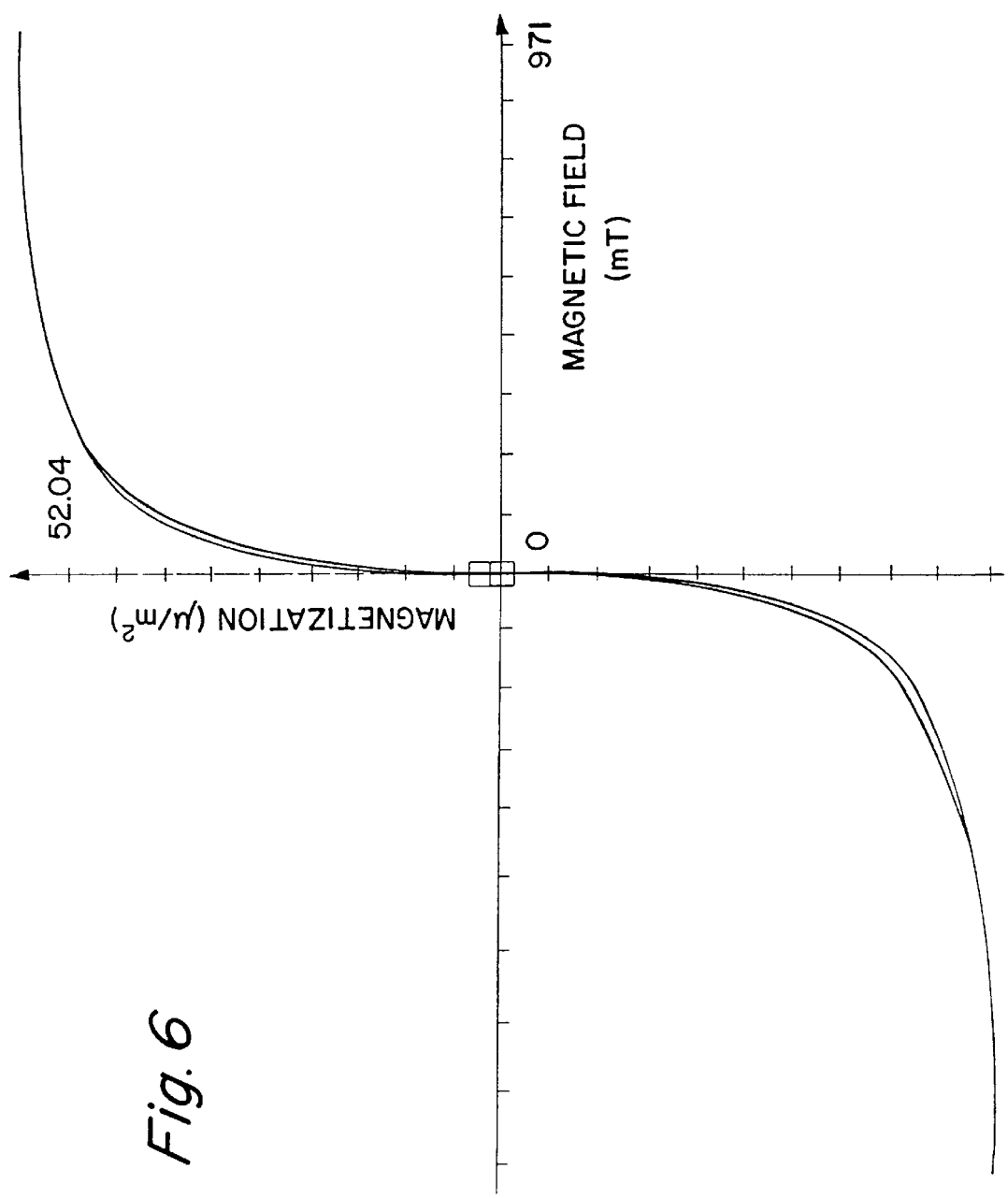
FIG. 6 is a plot of the magnetization curve for the composite particles of Example 11 below.

A dispersion of magnetite particles (Example 3, 0.5 g magnetite particles) was diluted with water (90 ml) and to this as added heparin (2 ml, Heparin 5000 IU/ml, Prod.no. F1NA, Nycomed Pharma, Oslo, Norway). The dispersion was sonicated, centrifuged and the supernatant filtered through 0.22 μm filter. A magnetization curve (FIG. 6) revealed that the heparin particles were superparamagnetic and they exhibit a mean hydrodynamic diameter of 65 nm. The size of the magnetite crystals was measured to be approximately 10 nm.

EXAMPLE 12—Heparin Analog Particles

Figure 7:
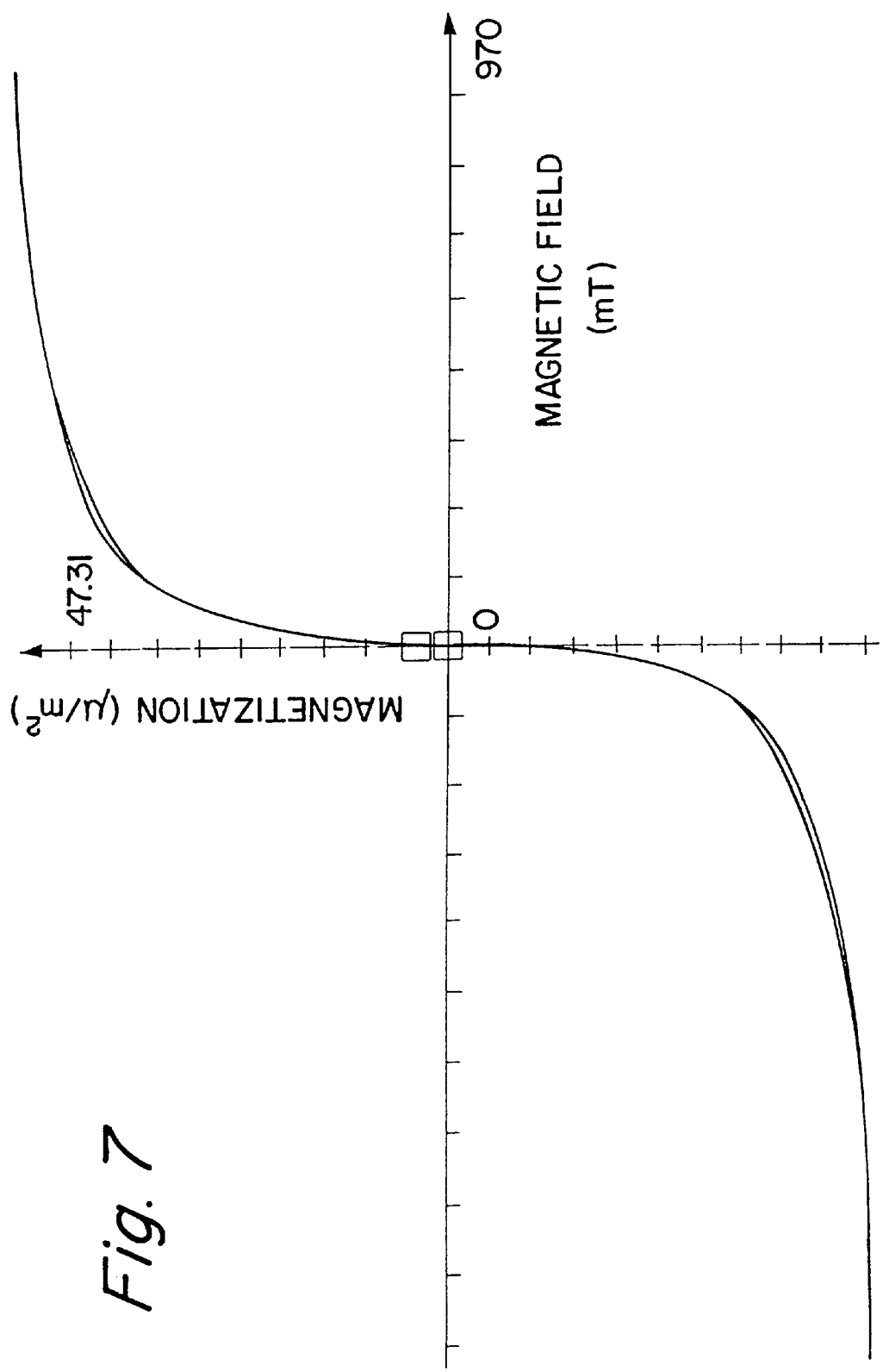
FIG. 7 is a plot of the magnetization curve for the composite particles of Example 12 below.

A dispersion of magnetite particles (Example 3, 0.23 g magnetite particles) was diluted with water (45 ml) and to this was added dermantan sulphate (30 mg, Sigma C-2413) dissolved in water. The dispersion was sonicated and centrifuged. The supernatant was collected. A magnetization curve (FIG. 7) revealed that the dermatan sulphate particles were superparamagnetic and they exhibit a mean hydrodynamic diameter of 77 nm.

EXAMPLE 13—Heparin Analog Particle

Figure 8:
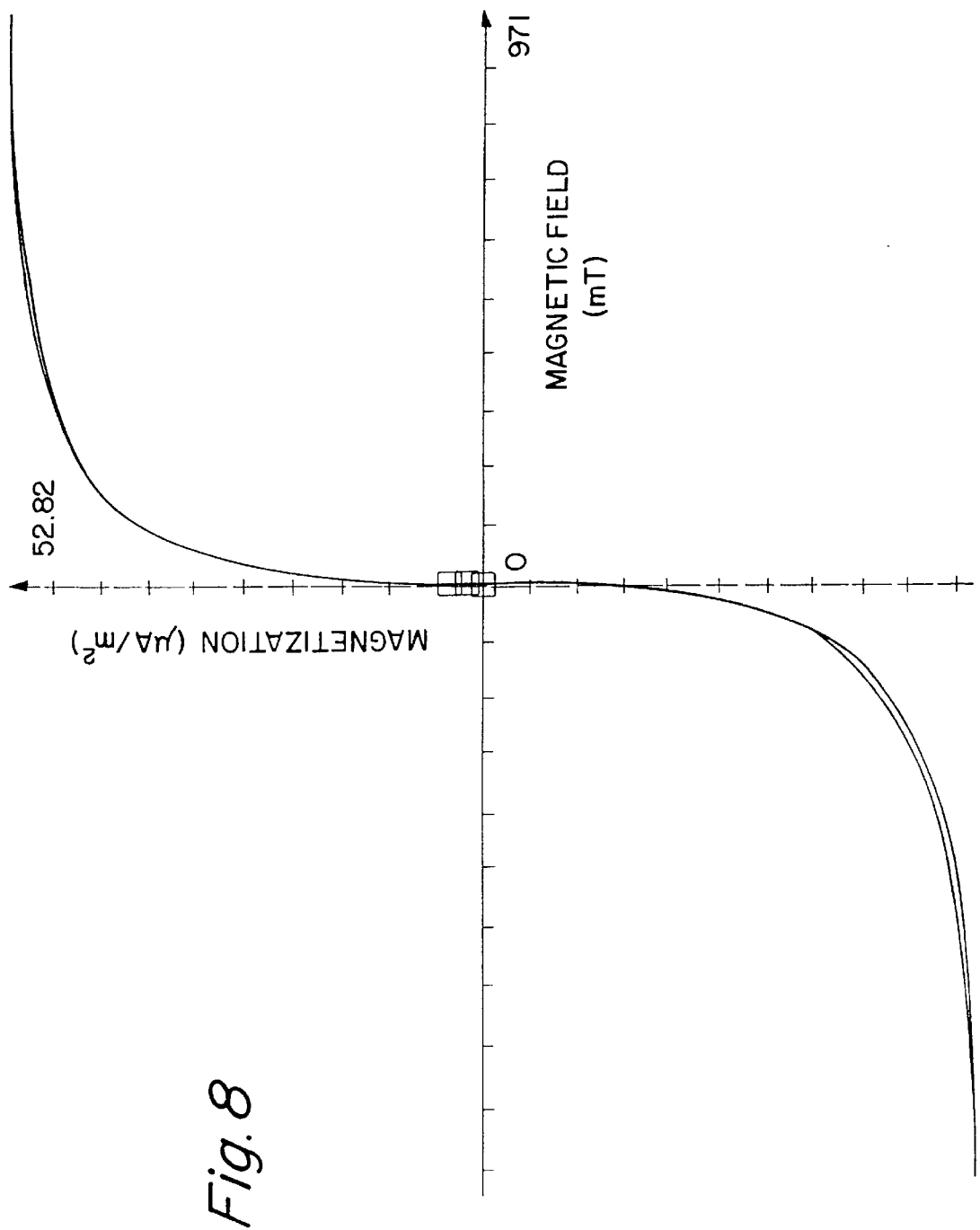
FIG. 8 is a plot of the magnetization curve for the composite particles of Example 13 below.

A dispersion of magnetite particles (Example 3, 0.25 g magnetite particles) was diluted with water (45 ml) and to this was added chondroitin-4-sulphate (50 mg, Sigma C-8529) dissolved in water. The dispersion was sonicated and centrifuged and the supernatant filtered through 0.2 μm filter. A magnetization curve (FIG. 8) revealed that the chondroitin-4-sulphate particles wore superparamagnetic and they exhibit a moan hydrodynamic diameter of 85 nm.

EXAMPLE 14—Heparin Analog Particles

A dispersion of magnetite particles (Example 3, 0.1 g magnetite particles) is diluted with water (15 ml) and to this is added heparan sulphate (20 mg, Sigma H-7641) dissolved in water. The dispersion is sonicated and centrifuged. The supernatant is collected.

EXAMPLE 15—Heparin Analog Particles

A dispersion of magnetite particles (Example 3, 0.1 g magnetite particles) is diluted with water (15 ml) and to this is added keratan sulphate (15 mg, Sigma K-3001) dissolved in water. The dispersion is sonicated and centrifuged. The supernatant is collected.

EXAMPLE 16—Carrageenan Particles

A dispersion of magnetite particles (Example 3, 0.5 g magnetite particles) was diluted with water (90 ml) and to this was added kappa-carrageenan (25 mg, Sigma C-1263) dissolved in water (2.5 ml). The dispersion was sonicated and centrifuged. The supernatant was collected. A magnetization curve revealed that the kappa-carrageenan particles wore superparamagnetic and they exhibit a mean hydrodynamic diameter of 490 nm.

EXAMPLE 17—Endogenous Carbohydrate Polymer Particles

A dispersion of magnetite particles (Example 3, 0.23 g magnetite particles) was diluted with water (45 ml) and to this was added hyaluronic acid (50 mg, Sigma H-4015) dissolved in water. The dispersion was sonicated, centrifuged and the supernatant filtered through 0.45 μm filter. A magnetization curve revealed that the hyaluronic particles were superparamagnetic and they exhibit a mean hydrodynamic diameter of 389 nm.

Example 18—Alginate Particles

Figure 9:
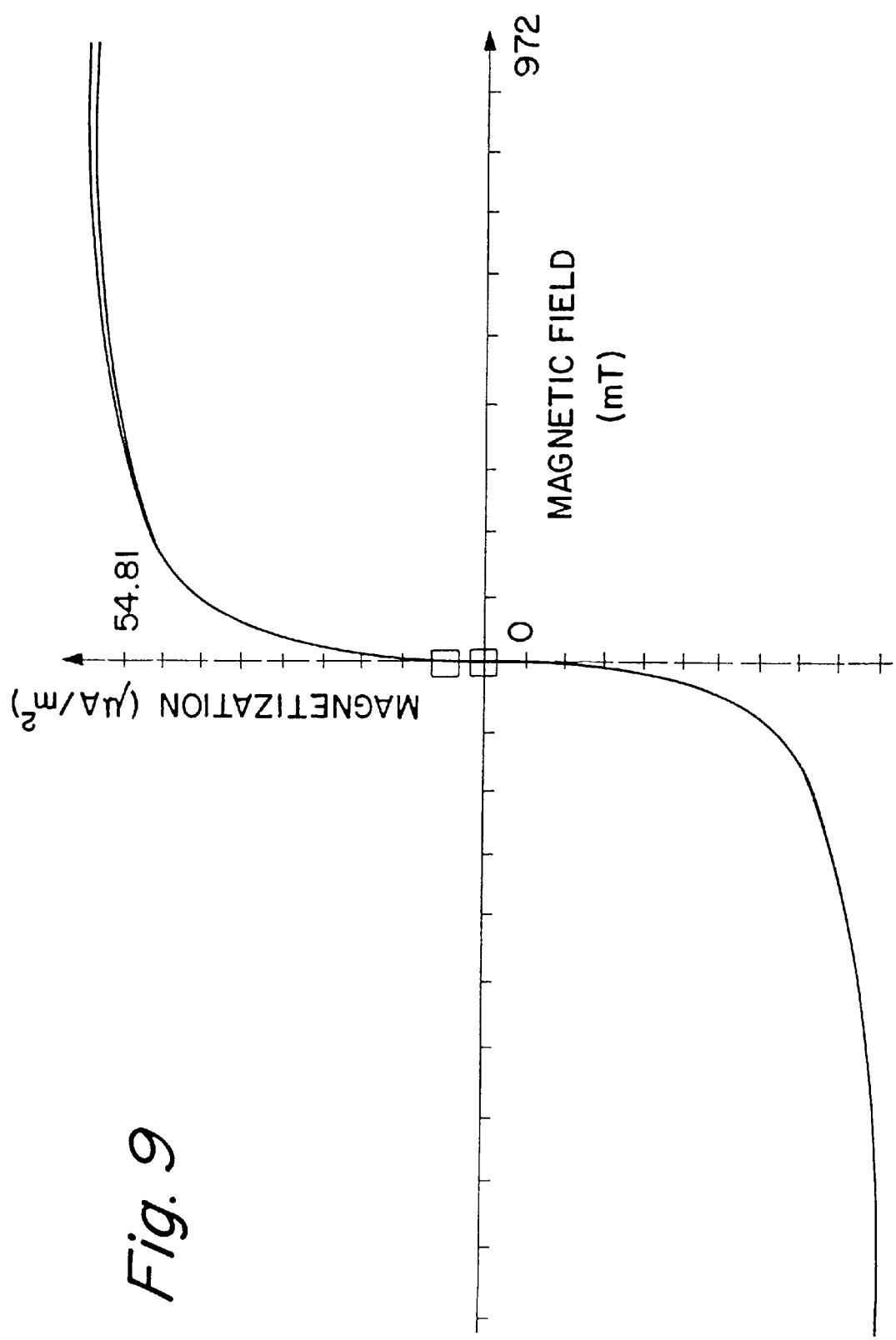
FIG. 9 is a plot of the magnetization curve for the composite particles of Example 18 below.

A dispersion of magnetite particles (Example 3, 0.5 g magnetite particles) was diluted with water (90 ml) and to this was added alginate (50 mg, Protanal LF 10/60, Pronova, Drammen, Norway) dissolved in water (5 ml). The dispersion was sonicated, centrifuged and the supernatant filtered through 0.22 μm filter. A magnetization curve (FIG. 9) revealed that the alginate particles were superparamagnetic and they exhibit a mean hydrodynamic diameter of 70 nm.

EXAMPLE 19—Alginate Particles

Figure 10:
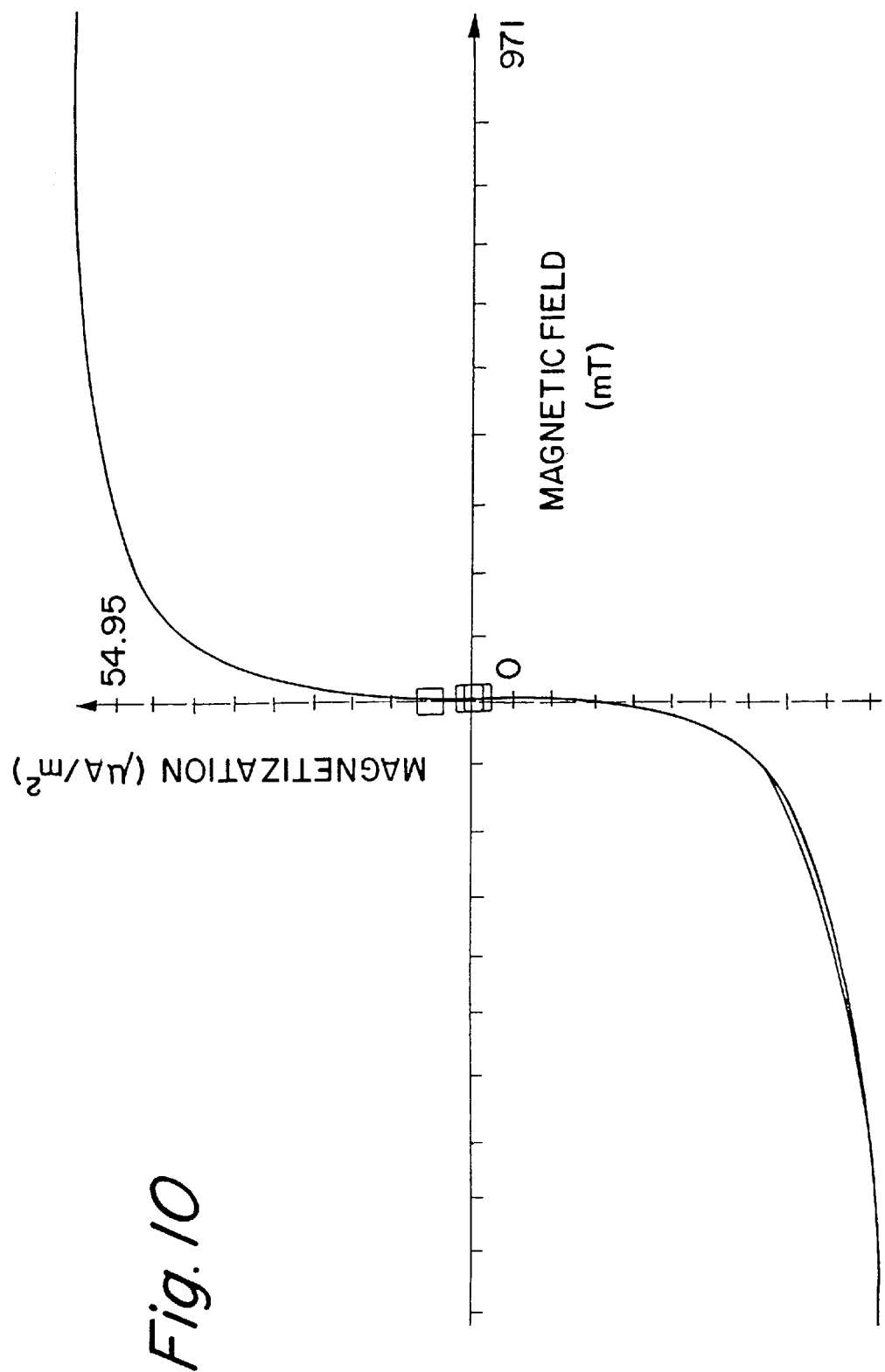
FIG. 10 is a plot of the magnetization curve for the composite particles of Example 19 below.

A dispersion of magnetite particles (Example 3, 0.5 g magnetite particles) was diluted with water (90 ml) and to this was added alginate (25 mg Protanal LF 60, Pronova, Drammen, Norway) dissolved in water (2.5 ml). The dispersion was sonicated, centrifuged and the supernatant filtered through 0.22 μm filter. A magnetization curve (FIG. 10) revealed that the alginate particles were superparamagnetic and they exhibit a mean hydrodynamic diameter of 65 nm.

EXAMPLE 20—Cellulose Derivative Particles

Figure 11:
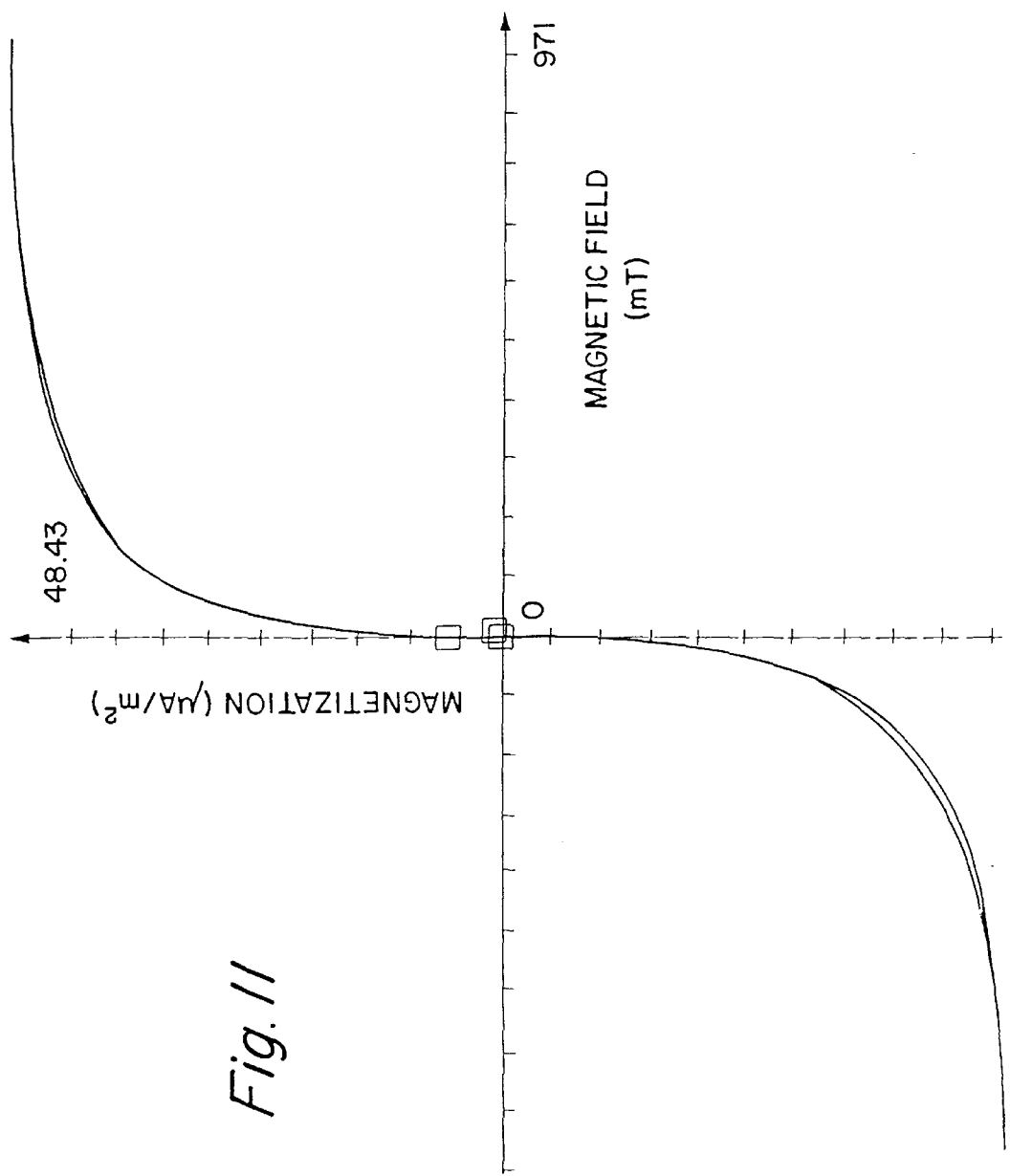
FIG. 11 is a plot of the magnetization curve for the composite particles of Example 20 below.

A dispersion of magnetite particles (Example 3, 0.5 g magnetite particles) was diluted with water (85 ml) and to this was added sodium carboxymethylcellulose (50 mg) dissolved in water (5 ml). The dispersion was sonicated, centrifuged and the supernatant filtered through 0.22 μm filter. A magnetization curve (FIG. 11) revealed that the carboxymethylcellulose particles were superparamagnetic and they exhibit a mean hydrodynamic diameter of 120 nm.

EXAMPLE 21—Chitosan Particles

Figure 12:
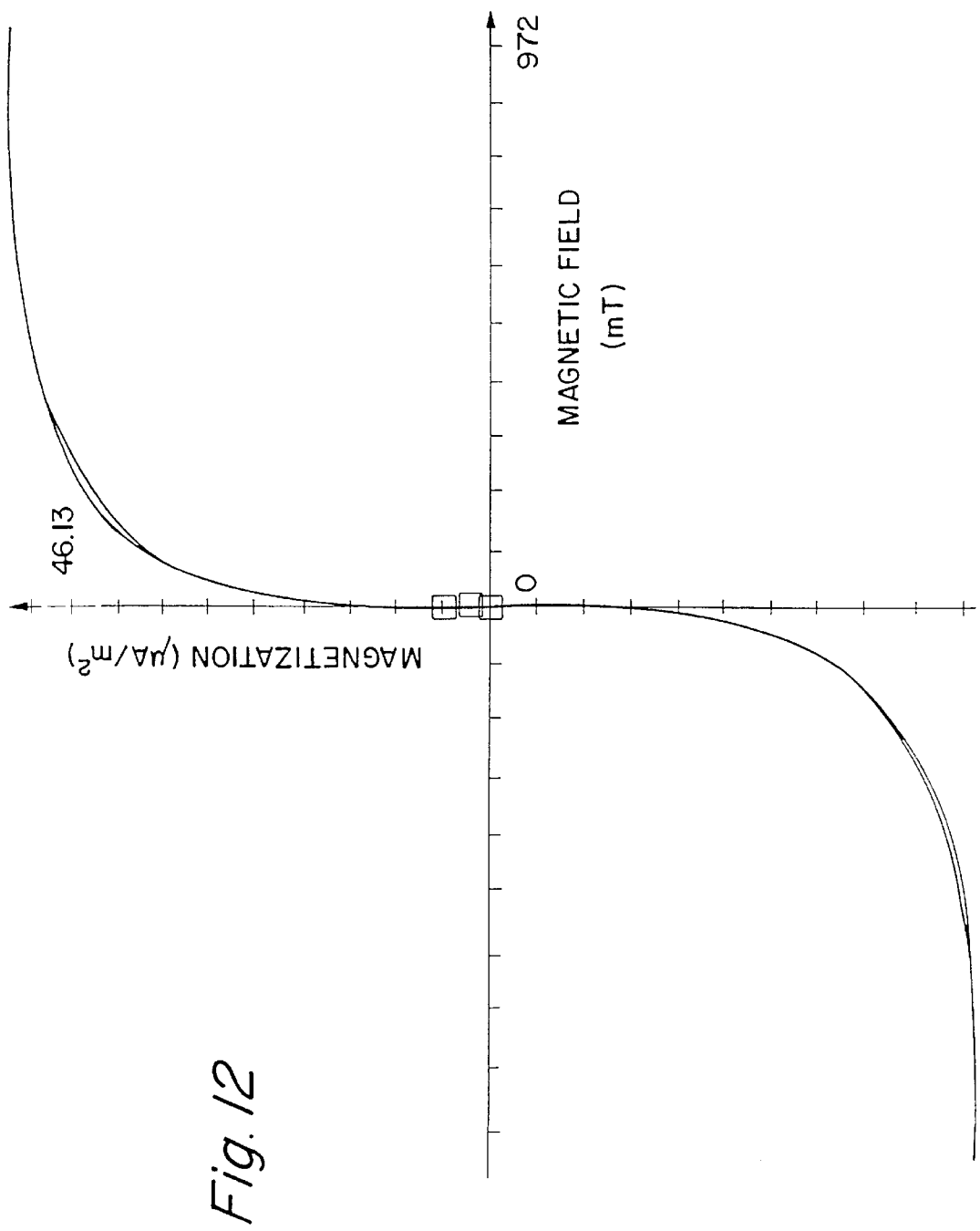
FIG. 12 is a plot of the magnetization curve for the composite particles of Example 21 below.

A dispersion of magnetite particles (Example 3, 0.5 g magnetite particles) was diluted with water (85 ml) and to this was added chitosan (50 mg, Pronova MV Chitosan Glutamate, Protan, Drammen, Norway) dissolved in water (5 ml). The dispersion was sonicated, centrifuged and the supernatant filtered through 0.45 μm filter. A magnetization curve (FIG. 12) revealed that the chitosan particles were superparamagnetic and they exhibit a mean hydrodynamic diameter of 97 nm.

EXAMPLE 22—Chitosan Particles

Chitosan (1.5 g, Pronova MV Chitosan Glutamate, Protan, Drammen, Norway) was dissolved in water (15 ml). At a temperature of 60° C., $FeCl_3.6H_2O$ (1.35 g) and $FeCl_2.4H_2O$ (0.81 g) was dissolved in the carbohydrate solution whereafter the mixture was slowly precipitated into 0.18M NaOH (100 ml) at 60° C. while sonicating. The sonication was allowed to continue for another 10 minutes followed by a centrifugation at 4000 rpm for 5 minutes. The supernatant was collected. A magnetization curve revealed that the chitosan particles were superparamagnetic and they exhibit a mean hydrodynamic diameter of 250 nm.

EXAMPLE 23—Agarose Particles

Figure 13:
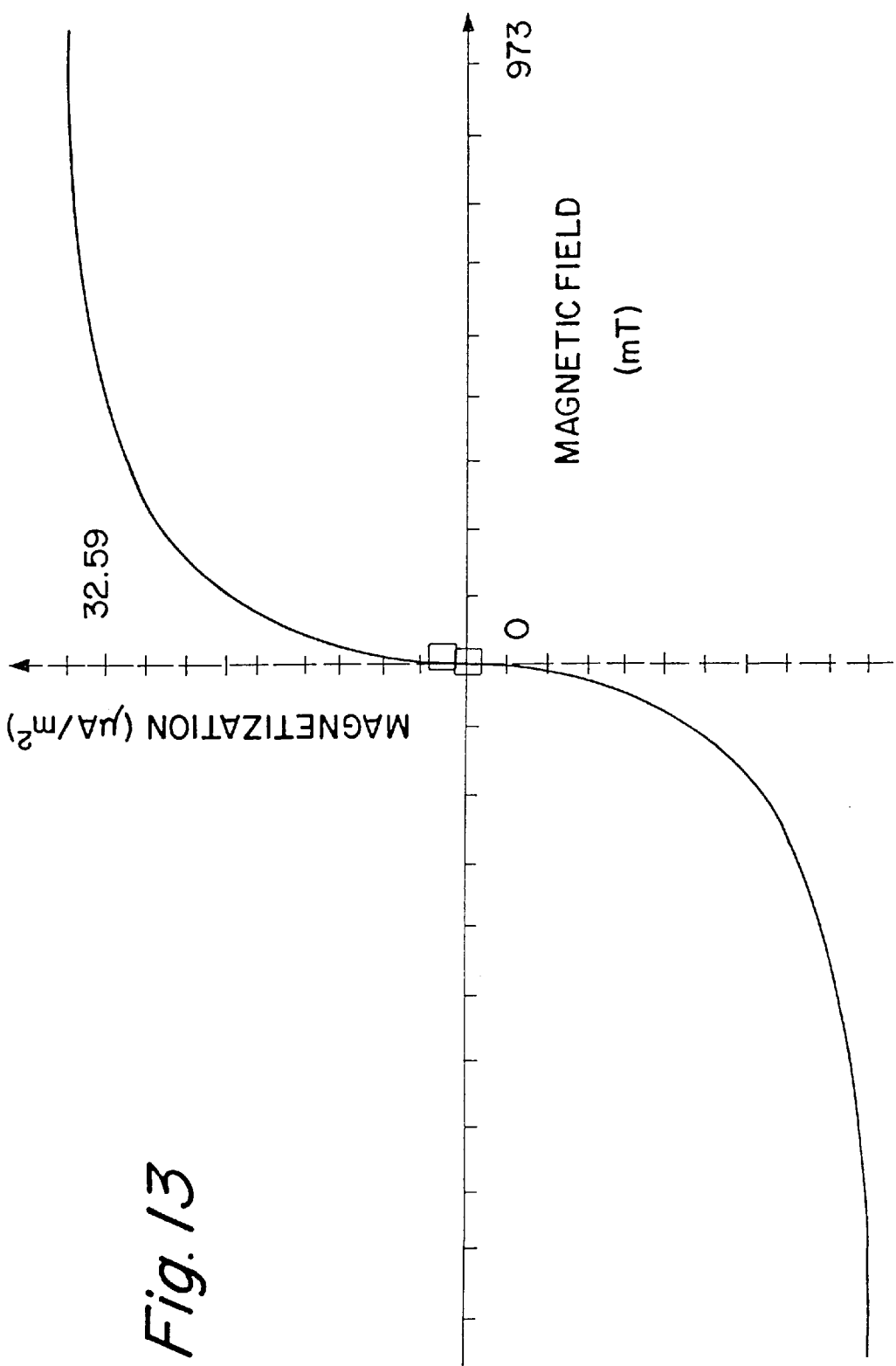
FIG. 13 is a plot of the magnetization curve for the composite particles of Example 23 below.

Agarose (1 g, Sigma A-9793) was dissolved in water (20 ml). At a temperature of 60° C., $FeCl_3.6H_2O$ (1.35 g) and FeCl$_2$.4H$_2$O (0.81 g) was dissolved in the carbohydrate solution whereafter the mixture was slowly precipitated into 0.18M NaOH (100 ml) at 60° C. while sonicating. The sonication was allowed to continue for another 10 minutes followed by a centrifugation at 4000 rpm for 5 minutes. The supernatant was collected. A magnetization curve (FIG. 13) revealed that the agarose particles were superparamagnetic.

EXAMPLE 24—Starch Particles

Figure 14:
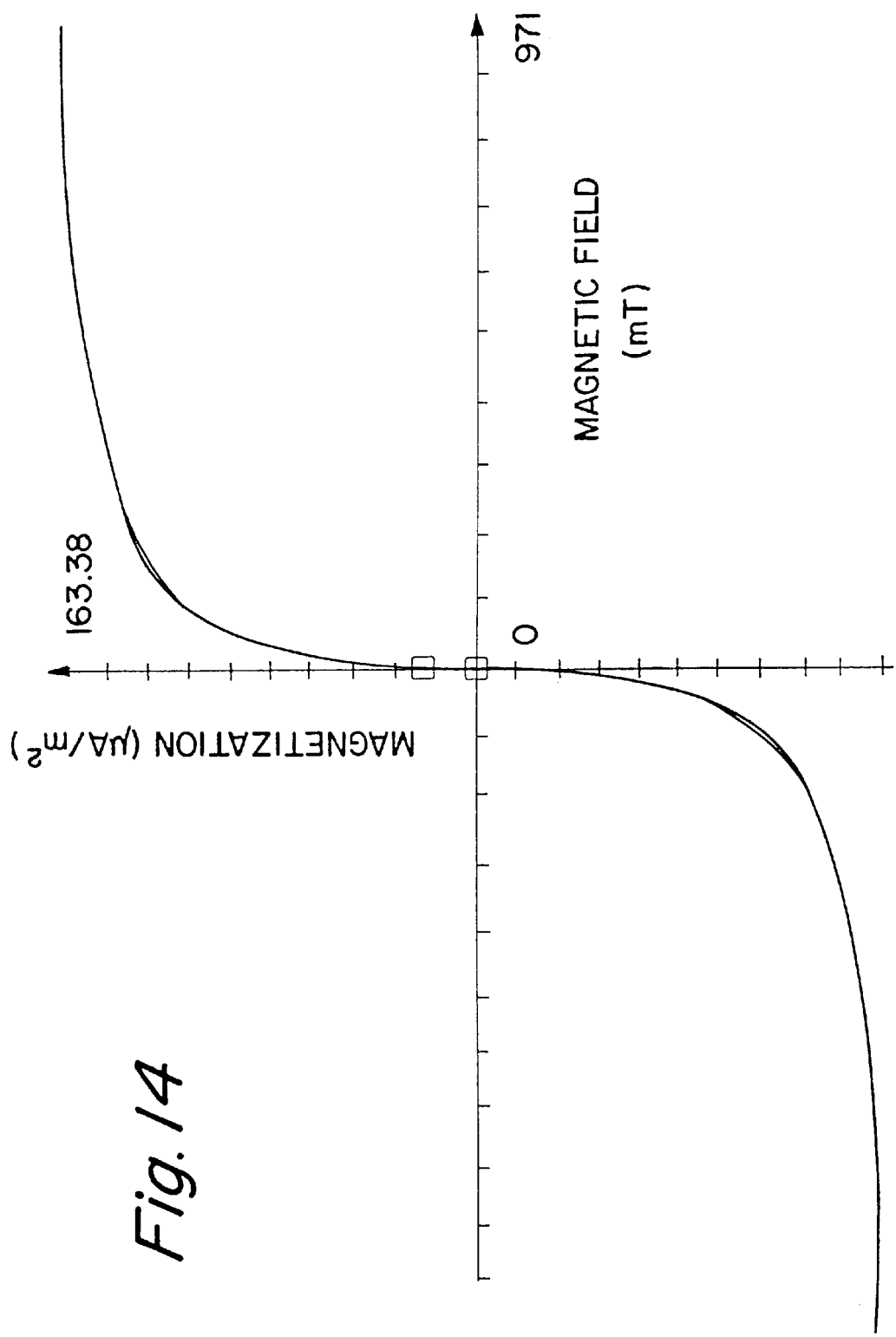
FIG. 14 is a plot of the magnetization curve for the composite particles of Example 24 below.

Starch (3 g, Reppe Glycose, Sweden) having a mean molecular weight of 70,000 was dissolved in water (10 ml). At a temperature of 60° C., FeCl$_3$.6H$_2$O (2.7 g) and FeCl$_2$.4H$_2$O (4.5 g) was dissolved in the carbohydrate solution whereafter the mixture was slowly precipitated into 1.2 M NaOH (50 ml) at 60° C. while sonicating. The sonication was allowed to continue for another 10 minutes followed by a centrifugation at 5000 rpm for 5 minutes. The supernatant was collected and dialysed against an aqueous solution of 0.9% NaCl. A magnetization curve (FIG. 14) revealed that the starch particles were superparamagnetic and they exhibit a mean hydrodynamic diameter of 450 nm. The size of the magnetite crystals was measured to be approximately 10 nm.

EXAMPLE 25—Dextrin Particles

Dextrin W50 (3 g, Stadex Ab, Malmö, Sweden) was dissolved in water (10 ml). At a temperature of 60° C., FeCl$_3$.6H$_2$O (1.35 g) and FeCl$_2$.4H$_2$O (0.81 g) was dissolved in the carbohydrate solution whereafter the mixture was slowly precipitated into 0.18M NaOH (100 ml) at 60° C. while sonicating. The sonication was allowed to continue for another 10 minutes followed by a centrifugation at 4000 rpm for 5 minutes. The supernatant was collected. A magnetization curve revealed that the dextrin particles were superparamagnetic and they exhibit a mean hydrodynamic diameter of 240 nm.

EXAMPLE 26—Dextrin Particles

Dextrin (200 mg, Awedex W25) and alfa-cyclodextrin (100 mg, Stadex AB, Malmö, Sweden) was mixed with a magnetite particles suspension in water (400 μl, size 10–20 nm Ferrofluid EMG 801 HGMS) and water (600 μl) at 70° C. for one hour. The mixture was emulsified in a medium consisting of vegetable oil (25 ml), Gafac PE-510 (1.25 g, Svenska Gaf AS, Stockholm, Sweden) and chloroform (5 ml) using a probe sonicator (diameter 15 mm) for 35 seconds while cooling on an icebath. The emulsion was slowly poured into acetone, containing 0.1% (w/v) Tween 80 while the solution was stirred at 1000 rpm. The precipitated microspheres were washed by centrifugation with 0.1% Tween 80/acetone (4×50 ml) and finally suspended in 1% Tween 80/acetone (2 ml) and dried at ambient temperature. A magnetization curve revealed that the dextrin particles were superparamagnetic and they exhibit a moan hydrodynamic diameter of 800 nm

EXAMPLE 27—Rat Liver Imaging

Using composite particles according to Examples 2 and 8 pre and post injection T$_2$-weighted spin echo MR images of the healthy rat liver were generated using a 2.4 Tesla MR scanner.

Figure 15A:
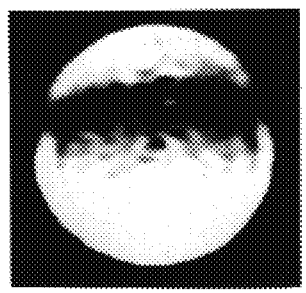
FIG. 15 is a $T_2$-weighted spin echo MR image of a rat, in cross-section through the abdomen at the liver.
Figure 15B:
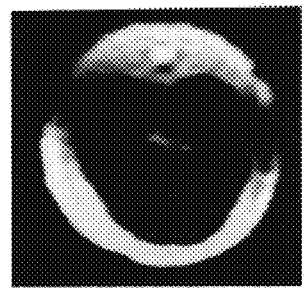
Figure 15C:
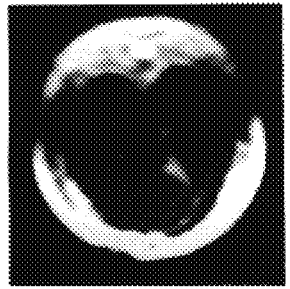
Figure 16A:
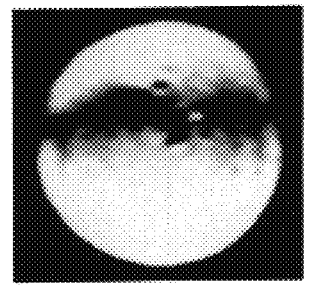
FIG. 16 is a $T_2$-weighted spin echo MR image of a rat, in cross-section through the abdomen at the liver.

FIGS. 15a and 16a are pre-injection (control) images. (The black band across the top of all the images of FIGS. 15 and 16 is an imaging artefact arising from sub-optimal performance of the scanner).

FIGS. 15b and 15c are post-injection images following dextran particle (Example 2) injection. The particles having reached the liver have suppressed the signal intensity therefrom with the result that the liver shows up as black. The white inclusion seen in FIG. 15c is probably due to a partial volume effect.

Figure 16B:
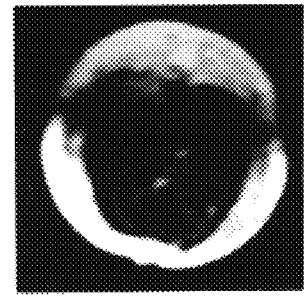
Figure 16C:
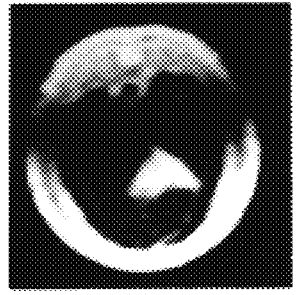

FIGS. 16b and 16c are similar post injection images for dextran derivative particles according to Example 8.

EXAMPLE 28—Rabbit Liver Tumour Imaging

Using composite starch particles prepared according to Example 24, pre and post injection T$_1$-weighted spin echo MR images of the rabbit liver were generated using a 2.4 Tesla scanner.

Figure 17A:
FIG. 17 is a $T_1$-weighted spin echo MR image of a rabbit again in cross section through the abdomen at the liver.

FIG. 17a is the pre-injection (control) image.

Figure 17B:

FIGS. 17b is the post injection image.

In both images, the liver is revealed as a generally dark area with paler patches. The post injection image shown signal suppression from the healthy areas of the liver where RES uptake of the particles is unimpeded and thus this image much more clearly delineates the tumorous areas (the approximately circular pale patches) than does the control image.

I claim:

1. In a method of contrast enhanced nuclear magnetic resonance diagnostic imaging which comprises administering into the vascular system of a subject a contrast enhancing amount of a nuclear magnetic resonance imaging contrast agent and generating an image of said subject, the improvement comprising administering as said contrast agent composite particles comprising a biotolerable, biodegradable, non-immunogenic carbohydrate or carbohydrate derivative matrix material containing magnetically responsive particles, said magnetically responsive particles being of a material having a Curie temperature and said composite particles being no larger than one micrometer in size.

2. A method as claimed in claim 1, wherein said composite particles are in the size range 0.010 to 1 μm.

3. A method as claimed in claim 1, wherein said composite particles comprise magnetically responsive particles of magnetite.

4. A method as claimed in claim 1, wherein said composite particles comprise magnetically responsive particles which are superparamagnetic.

5. A method as claimed in claim 3, wherein said composite particles contain 10–20 nm magnetite particles.

6. A method as claimed in claim 1, wherein said matrix material is a polymeric material.

7. A method as claimed in claim 6, wherein said composite particles comprise as said matrix material a material selected from the group consisting of dextran, carbohydrate polymers of types which occur naturally in the body, and derivative thereof.

8. A method as claimed in claim 6, wherein said composite particles comprise as said matrix material a material selected from the group consisting of starch, chitosan, carrageenan, heparin, dextran, dextrin and derivatives thereof.

9. A method as claimed in claim 6, wherein said composite particles comprise dextran as said matrix material.

* * * * *